United States Patent [19]
Kiritchenko

[11] Patent Number: 6,075,217
[45] Date of Patent: Jun. 13, 2000

[54] COLOR DETECTION APPARATUS

[75] Inventor: Alexandre Ivanovitch Kiritchenko, Zaporozhye, Ukraine

[73] Assignee: Chipper 2000 Limited, United Kingdom

[21] Appl. No.: 08/875,368

[22] PCT Filed: Jan. 23, 1996

[86] PCT No.: PCT/GB96/00115

§ 371 Date: Jul. 24, 1997

§ 102(e) Date: Jul. 24, 1997

[87] PCT Pub. No.: WO96/23281

PCT Pub. Date: Aug. 1, 1996

[30] Foreign Application Priority Data

Jan. 24, 1995 [GB] United Kingdom .................... 9501359
Apr. 28, 1995 [GB] United Kingdom .................... 9508633

[51] Int. Cl.[7] .................................. B07C 5/342; G01J 3/46
[52] U.S. Cl. .......................... 209/582; 209/587; 209/938; 250/226; 356/416; 356/425
[58] Field of Search .................................. 209/576, 577, 209/580, 581, 582, 587, 938; 250/221, 223 R, 226; 356/73, 411, 416, 425

[56] References Cited

U.S. PATENT DOCUMENTS 5,265,732  11/1993  Long ........................................ 209/580
5,325,169   6/1994  Nakamoto et al. .................. 209/581 X
5,502,559   3/1996  Powell et al. ........................ 209/582 X

FOREIGN PATENT DOCUMENTS 61-110016   5/1986  Japan ..................................... 209/582

*Primary Examiner*—Tuan N. Nguyen
*Attorney, Agent, or Firm*—Watts, Hoffmann, Fisher & Heinke Co., L.P.A.

[57] ABSTRACT

A chip sorting apparatus is disclosed. The apparatus includes an article transport mechanism, a light source positioned to direct light across surfaces of transported articles, and a detector positioned to detect light reflected from such surfaces and emit signals each indicative of a spectrum of light reflected by one such article as such articles are transported. A signal analyzer compares detector signals with stored data representative of the colors of articles of a set of articles being sorted. The analyzer emits article identifying signals reflective of such comparison. The apparatus also includes a sorter which is responsive to such identifying signals and directs identified articles from the transport mechanism into appropriate ones of a set of collection stations. A method of sorting a set of articles according to color is also disclosed.

9 Claims, 5 Drawing Sheets

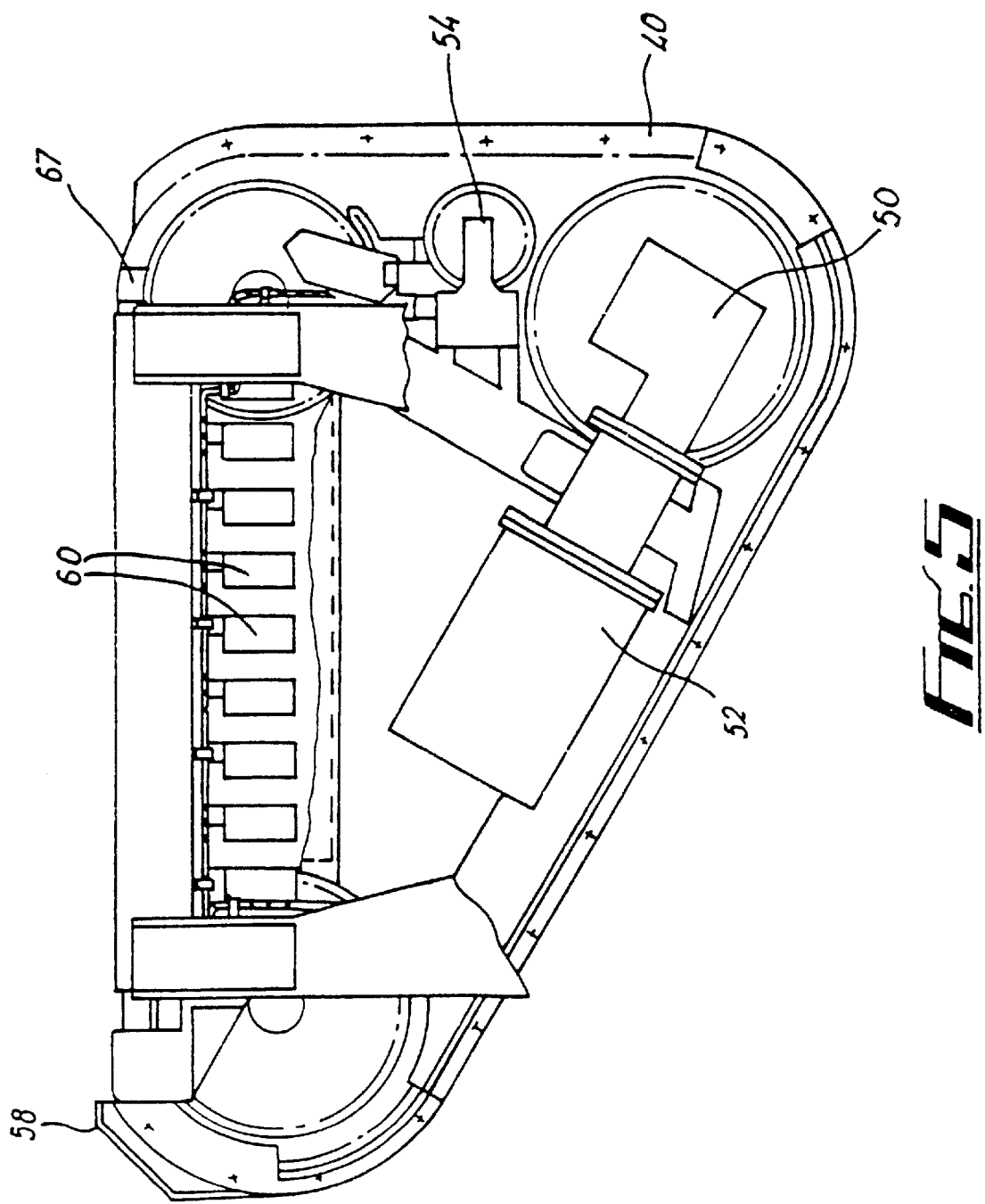

COLOR DETECTION APPARATUS

This invention concerns colour detection apparatus, particularly but not exclusively apparatus for sorting different coloured articles, and especially apparatus for sorting different coloured gambling chips.

Prior arrangements for automatically sorting coloured gambling chips have generally used a plurality of photocells, usually three cells each having a respective filter to detect respectively red, yellow and green light. This arrangement is relatively unsophisticated and problems can occur in detecting different coloured chips and especially relatively similar colours. Particular difficulties can also be encountered when some chips of a particular colour have become faded and/or dirty relative to other chips due perhaps to the chips being of different ages. Colour variations can also occur between different batches of a particular colour chip. Further difficulties have also been experienced with chips with different coloured faces on each side, or chips bearing ordered or random patterns.

When the 'colour of an article' is referred to in this specification, this may include an article of more than one colour and/or one which bears a pattern.

According to the present invention there is provided colour detection apparatus, the apparatus comprising means for detecting light intensity substantially across the visible spectrum and means for comparing the read light intensity relative to a previously read light intensity substantially across the visible spectrum.

Means are preferably provided for comparing the read light intensity with previously read light intensities for one or more known colours.

Means are preferably provided for reading the light intensity at a plurality of closely spaced intervals across the visible spectrum. The light intensity can preferably be read at over twenty spaced intervals, desirably over fifty spaced intervals, and more particularly substantially sixty four spaced intervals.

Preferably means are provided for splitting the light into one or more spectra.

Diffraction means may be provided for splitting the light into one or more spectra, and desirably a diffraction grid is provided. Means are preferably provided for focusing light onto the diffraction grid.

Where the light is split into more than one spectra, the apparatus is preferably arranged to read the light intensity across respective parts of adjacent spectra, desirably with the red end of a one spectra being read along with the blue end of a larger spectra. The apparatus may comprise a visible detector capable of measuring light intensity at a plurality of closely spaced intervals, for measuring the respective light intensities across the spectrum or the respective parts of each spectra.

The invention also provides apparatus for detecting the colour of an article, the apparatus comprising colour detection apparatus according to any of the preceding six paragraphs.

The apparatus preferably comprises means for shining light onto the article.

The apparatus is preferably arranged such that the colour is read for at least part of the article. Means are preferably provided for moving the article relative to the detection apparatus during colour detection, such that colour is read across at least part of the article.

The detection apparatus may be arranged to record the colour detected, i.e. the intensity and frequency, and the positioning of the article, so as to detect changes in colour and/or pattern across the article. The apparatus preferably comprises means for differentiating the colour detected relative to the position on the article so as to indicate colour changes.

The apparatus preferably also comprises means for comparing the colour detected with a plurality of previous colour detections of articles, with the articles at different orientations.

The apparatus may also be arranged to include the detected colour of an article in subsequent comparisons, whereby to update the apparatus if for example the colour of article is changing due to dirt, fading or different light conditions.

The invention further provides apparatus for sorting different colour articles, the sorting apparatus comprising apparatus for detecting the colour of an article according to any of the preceding four paragraphs, and means for automatically directing the article to a required location in response to the colour detected by said colour detecting apparatus.

The apparatus may comprise means for allocating values to articles, and inputting into the apparatus which colour or colours of article have each value; and means for directing articles of each value to a respective required location.

The apparatus preferably also comprises means for recording how many articles of each value and/or colour have been sorted by the apparatus over a given time period.

The sorting apparatus preferably comprises means for automatically supplying articles to the colour detecting apparatus. A receptacle may be provided for the articles, and from which the supply means takes the articles. A movable continuous member may be provided extending through the receptacle for supplying the articles to the colour detecting apparatus.

A plurality of article holders may be provided on the continuous member. Means may be provided for providing a required tension in the continuous member, and said member may comprise a chain.

The sorting apparatus preferably comprises means for automatically directing an article to a respective one of a plurality of locations in response to the colour detected.

The sorting apparatus may comprise a plurality of engagement members respectively operable in response to the colour detected to move an article off a one of the holders such that the article is directed to a respective required location. The engagement members may be located substantially in line downstream of the colour detecting apparatus relative to the continuous member, desirably with a plurality of respective receiving areas on the opposite side of the continuous member thereto. The engagement members may be selectively engageable with sprung pusher members on the article holders for removing an article therefrom.

The sorting apparatus is preferably arranged such that articles are directed to a respective location if their colour corresponds to the colour of an article whose colour has been previously detected and recorded during programming of the apparatus. The apparatus may be arranged such that a range of shades and/or intensities of a particular colour article can be detected and recorded during programming, to set tolerances for an article being detected as corresponding to a particular colour. Alternatively, or in addition, means may be provided to permit the tolerance of the range of colours considered as corresponding, to be varied.

The sorting apparatus is preferably arranged such that all articles which have not previously been directed to a respective required location subsequent to passing the colour detection apparatus, are automatically directed to a final location or returned to the receptacle. An end engagement member is preferably engageable with each article holder downstream of the required locations for receiving articles.

A limited clearance may be provided either side of the continuous member upstream of the colour detecting apparatus to ensure that articles are correctly aligned in the article holders prior to passing said apparatus, and that only one article is located in each holder.

Means are preferably provided in the apparatus for electrostatically collecting dust and dirt.

The dust collecting means is preferably electrostatically charged by virtue of movement of the continuous member.

The dust collecting means preferably comprises a collecting member of a readily electrostatically chargeable material, for example nylon.

The collecting member may comprise the end engagement member, which may comprise a cam engageable with the pusher members on the article holders, said engagement causing the electrostatic charging of the end engagement member.

Means may be provided for automatically stopping movement of the continuous member if resistance to movement thereof above a predetermined limit is detected. The sorting apparatus may be arranged such that movement of the continuous member is reversed for a short period following detection of such increased resistance with a view to clearing any blockage of articles.

The sorting apparatus is preferably computer controlled and means may be provided for converting analog signals received from the colour detection apparatus to digital signals for comparison.

Still further according to the present invention there is provided apparatus for sorting different colour gambling chips, the apparatus being according to any of the preceding twenty two paragraphs.

The chip sorting apparatus preferably comprises a rack or other chip holder into which the chips are delivered, with each colour chip being delivered to a respective part thereof.

The invention further provides a method for checking the colour of an article, the method comprising detecting the colour intensity of the article substantially across the visible spectrum, and comparing the read colour intensity with a previously read colour intensity substantially across the visible spectrum of an article of a known colour to ascertain whether the checked article is of the same colour.

The read colour intensity is preferably compared relative to previously read colour intensities of an article at a plurality of different orientations and/or a plurality of articles.

The light intensity is preferably read at a plurality of closely spaced intervals across the visible spectrum. The light intensity is preferably read at over twenty spaced intervals, desirably over fifty spaced intervals, and more particularly substantially sixty four spaced intervals.

Light is preferably shone on the articles to be detected, and the light reflected from the articles is preferably split into one or more spectra.

Where the light is split into more than one spectra, the light intensity is preferably read across respective parts of adjacent spectra, desirably with the red end of a one spectra being read along with the blue end of a larger spectra.

The colour intensity is preferably read across at least part of the surface of the articles. The colour intensity may be detected relative to the location on the articles. The colour intensity read is preferably differentiated relative to the location on the article so as to indicate colour changes. Only colour changes may be stored from previously checked articles, such that only colour changes are compared.

The previously read colour intensities are preferably automatically updated if variations are noted in subsequent colour intensities for articles of the same colour.

Tolerances may be set for deciding whether an article is of the same colour as a previously detected article, and the tolerances may be adjustable.

The method is preferably computer controlled.

An embodiment of the present invention will now be described by way of example only with reference to the accompanying drawings, in which FIG. 1 is a diagrammatic cross-sectional view of colour detecting apparatus according to the invention;

FIG. 5 is a diagrammatic rear view of part of the apparatus of FIG. 3.

Figure 1:
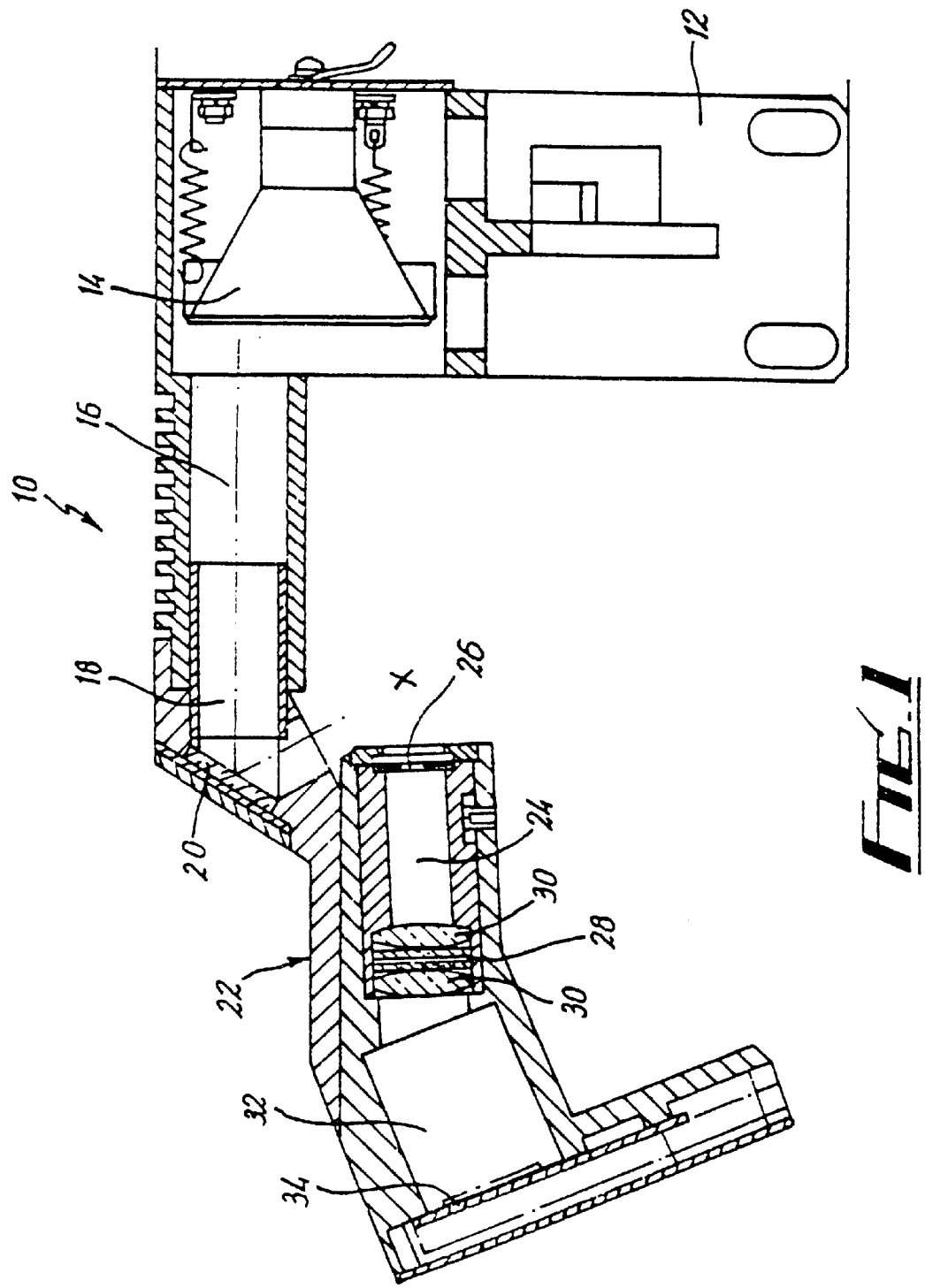
Figure 2:
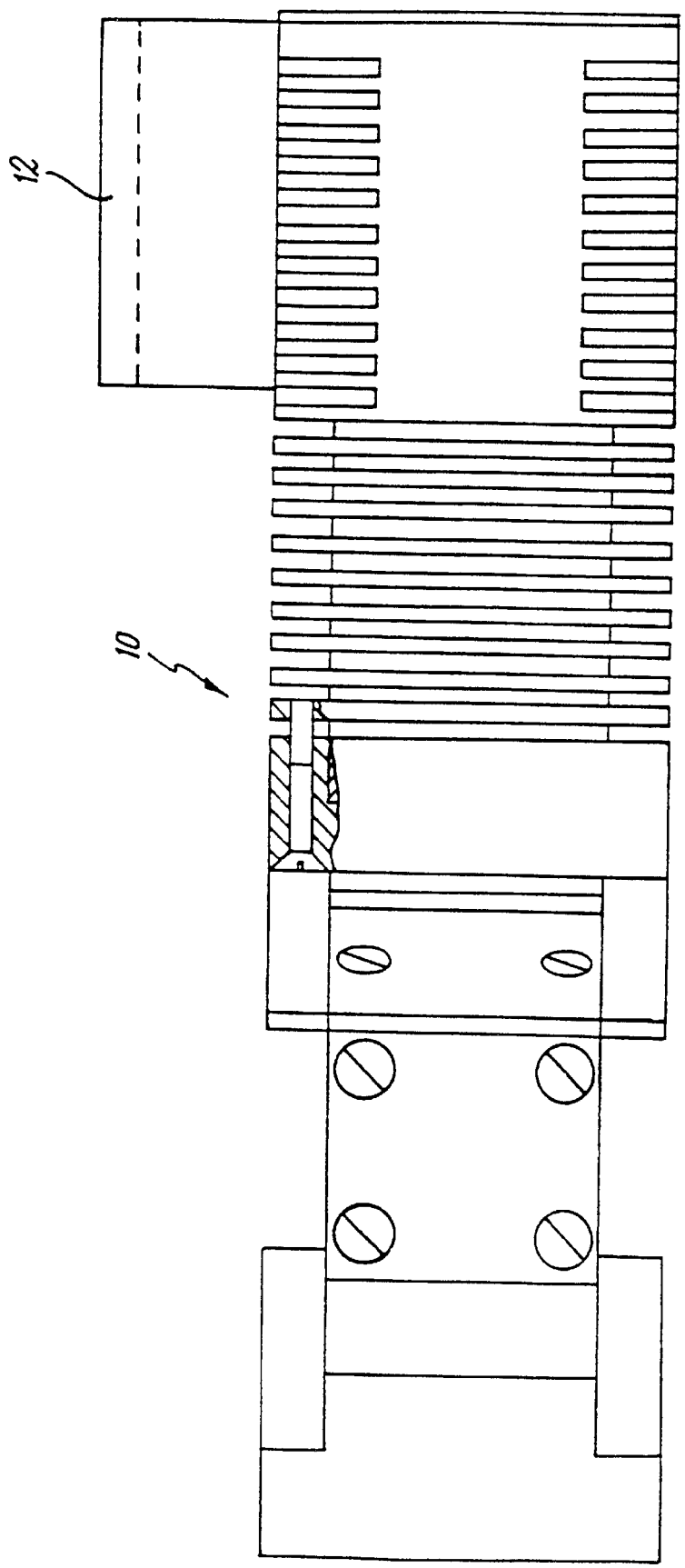
FIG. 2 is a plan view of the apparatus of FIG. 1.

FIGS. 1 and 2 show colour detecting apparatus 10 suitable for detecting for example the colour of a gambling chip located approximately at X. The apparatus 10 comprises a mounting bracket 12 above which is located an electric lamp 14. A passage 16 is located in front of the top part of the lamp 14 to receive light therefrom.

A collimator 18 is provided at the far end of the passage 16. Beyond the collimator 18 is a downwardly angled mirror 20 which directs light from the lamp 14 downwardly to X. The mirror 20 is located in a housing 22 which extends beyond X. The housing 22 mounts a further passage 24 beyond and facing X, with a narrow opening 26 on the end thereof facing X. A diffraction grid 28 is provided towards the other end of the passage 24 between two convex lenses 30. A broader passage 32 extends at a downward inclination from the end of the passage 24 with a sixty four position visible detector 34 at the far end thereof.

Figure 3:
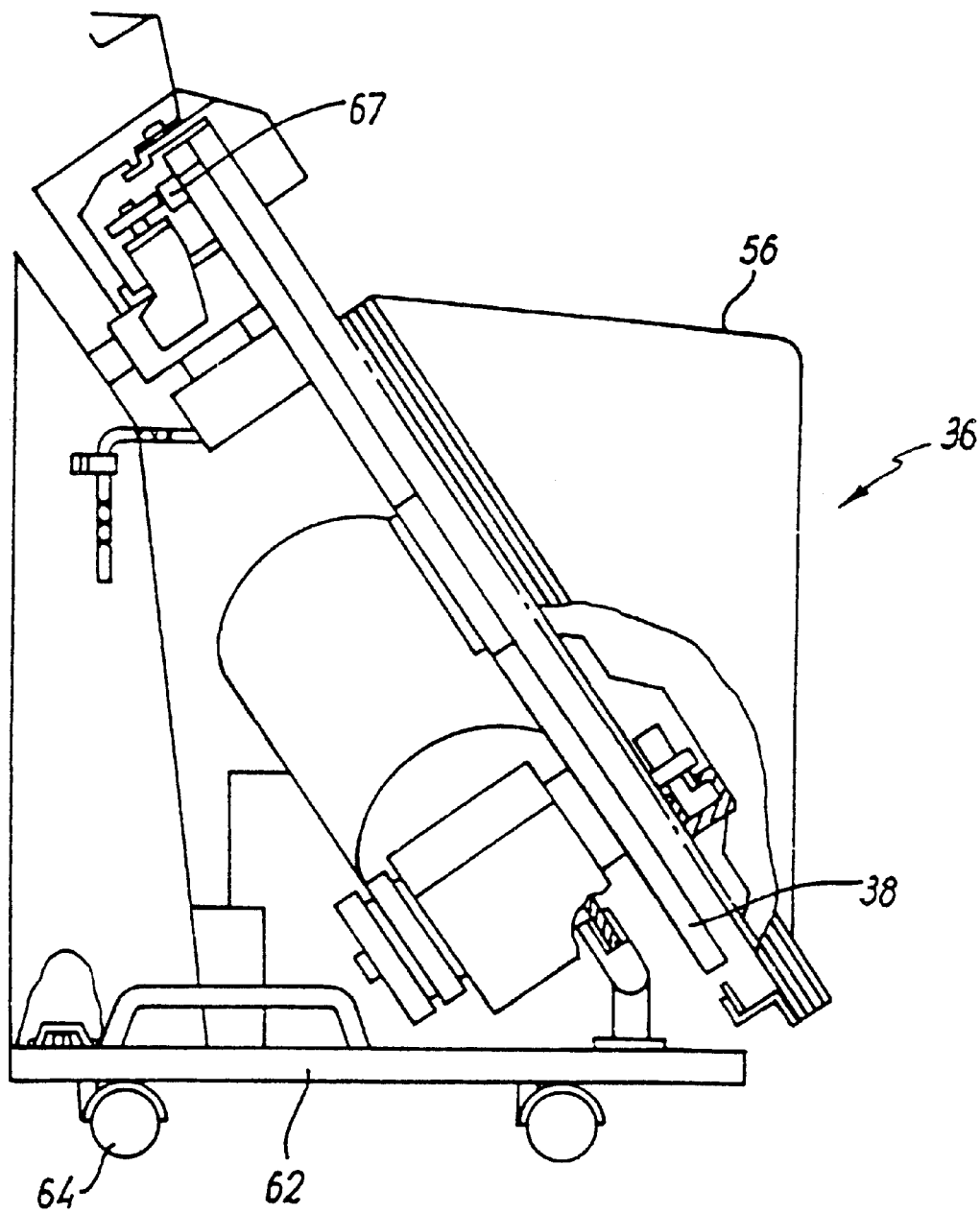
FIG. 3 is a diagrammatic partially cut-away side view of apparatus for sorting gambling chips according to the invention and incorporating the apparatus of FIG. 1.
Figure 4:
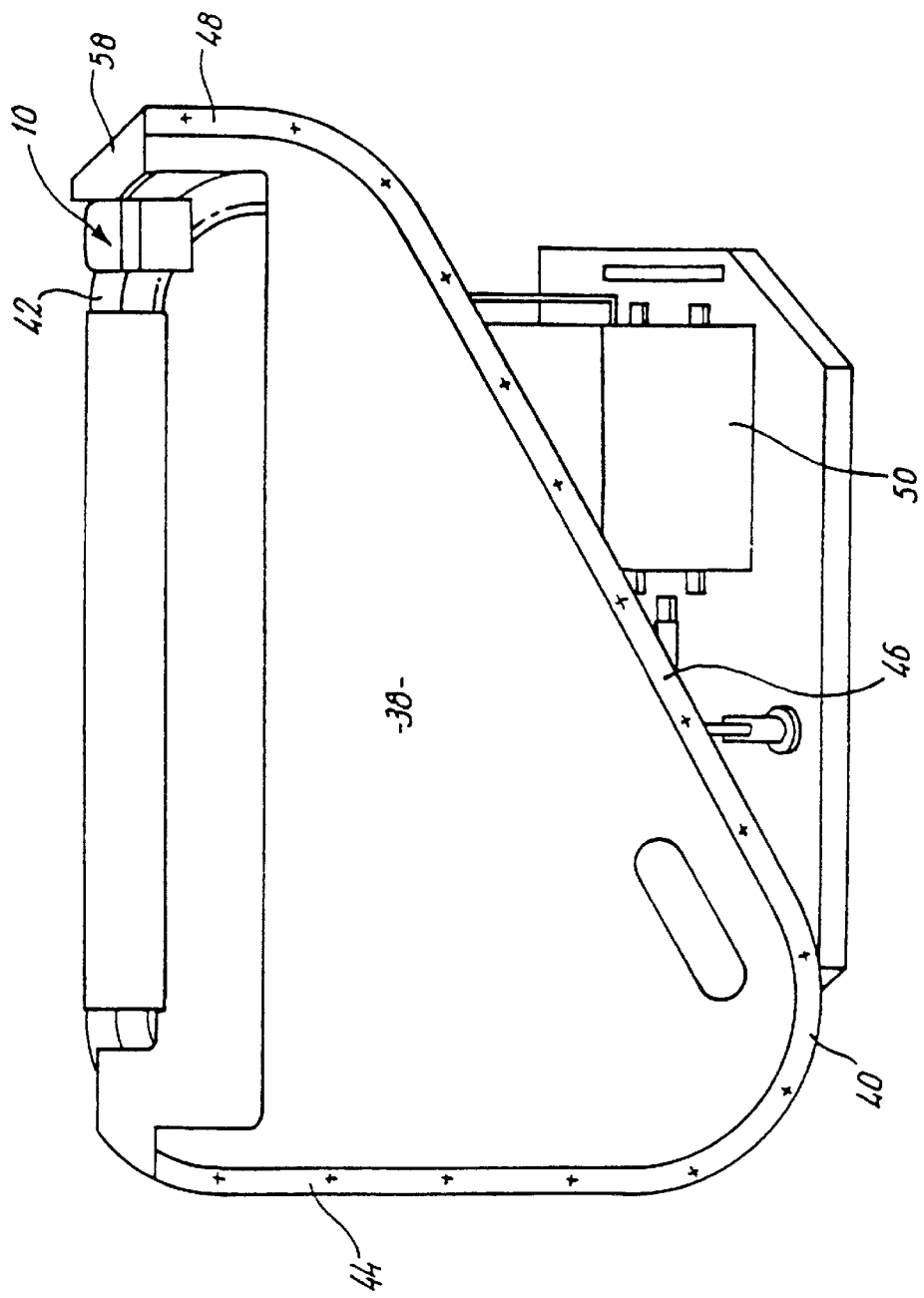
FIG. 4 is a diagrammatic front view of part of the apparatus of FIG. 3.

FIGS. 3–5 show a gambling chip sorting apparatus 36. The apparatus comprises a plate 38 inclined downwardly and outwardly at a relatively steep gradient. A continuous member in the form of a chain 40 extends in a loop over the plate 38 substantially adjacent the edge thereof. The chain 40 is movable in an anti-clockwise direction from a horizontal upper pass 42, to a long vertical down pass 44, to a gradual upwardly inclined portion 46 to a short vertically upwards extending portion 48. The chain 40 is drivable by a motor 50 through a gearbox 52. An automatic chain tensioning device 54 is provided in engagement with the chain 40. A plurality of holders (not shown) are provided on the chain 40 with a suitable size circular recess in each for carrying a gambling chip. A sprung pusher member is provided in each holder and arranged so as to eject a chip from the holder when pushed against the spring force.

An open topped bin 56 with substantially vertical sides is provided on the front side of the plate 38 with the chain 40 running through the interior thereof. A paddle (not shown) may be provided in the bin adjacent the connection between the pass 44 and portion 46 to direct chips into the holders.

A plate 58 is provided spaced from the plate 38 a short distance from the chain 40 such that there is limited clearance between the plate 58 and holders passing thereby. The plate 58 thereby ensures that any chips carried by the holders are in correct alignment, and only one chip can be carried by each holder. The plate 58 is located at the far right hand end as shown in FIG. 4 of the upper pass 42. Immediately downstream of the plate 58 is the measuring apparatus 10. Downstream of the apparatus 10 are ten chip directing stations (not shown in detail). Each of the stations comprises a solenoid 60 operated finger (not shown) engageable with the sprung pusher members on the holders to push a chip off the holder. The fingers are generally located behind and slightly above the plate 38 such that chips are pushed in a direction out of the page as shown in FIG. 4.

Opposite each of the fingers and extending in a direction out of the page as shown in FIG. 4, are a plurality of racks (not shown) to accept the different chips. The apparatus 36 is arranged such that if a chip has not been urged from a holder at a one of the directing stations, either the chip is urged off the holder at the most downstream directing station, or the chip is urged back into the bin 66 before leaving the upper pass 42.

To provide this final ejection a nylon cam member 67 (FIGS. 3 and 5) is provided downstream of the chip directing stations. The cam member 67 is engageable with each sprung pusher member on the article holders to eject any remaining chips therefrom.

The cam member 67 provides a dual roll in that it also collects dust and dirt in the apparatus 36 by electrostatic attraction. The regular enagement of the pusher members, during operation of the apparatus 36, against the member 67 causes an electrostatic charge thereon. Dirt/dust can readily be removed from the member 67 when the apparatus 36 is switched off.

The apparatus 36 is mounted on a base 62 with wheels 64 to enable ready movement thereof for example to adjacent a roulette table or elsewhere.

In use, the apparatus 36 is programmed as follows. Each directing station is programmed to a relevant colour chip by detecting and recording the colour of a sample chip placed in the apparatus 10. A plurality of sample chips of each colour may be detected to provide a range of recordings to set tolerances to accept variations of intensity or tone etc. for a particular colour. If required it may be possible to manually adjust the tolerance for any or all colours. Once each directing station has been programmed to be actuable for a respective colour, the apparatus 36 is ready for operation.

Used chips are directed into the bin 56. The chips are taken up by the holders carried by the chain 40, perhaps with the assistance of the paddle. The chips are then carried by the chain 40 past the plate 38 to ensure correct alignment.

The colour of the chips is then detected by the apparatus 10 in the following manner. Light from the lamp 14 is focused in the collimator 18 and reflected onto the chip by the mirror 20. Colour is detected as chips move past the apparatus 10 such that colour is detected over a rectangular area on the chips. Light reflected from the chip 20 passes through the opening 26 and subsequently through the lenses 30 and diffraction grid 28 sandwiched therebetween. Light passing through the grid 28 is diffracted to produce a plurality of spectra to be read by the detector 34.

The detector 34 is arranged to measure light intensity of the red end of a first spectra and the blue end of an adjacent further larger spectra. The detector 34 is arranged to measure across the whole visible spectrum though in two different spectra. Measuring the larger spectra for the blue end permits a greater number of readings in this area where accurate measurements are more typically difficult to obtain. The detector 34 measures the light intensity at sixty four positions across the respective spectra, and produces an analog signal which is sent to a control computer (not shown).

The control computer converts the analog signal to a digital signal and compares this with the signals previously recorded for the colours of the chips measured during programming. If the colour of a chip being measured corresponds within the tolerances of a one of the previously programmed coloured chips, a signal is sent to the appropriate directing station such that when the corresponding holder is adjacent the respective station, the finger is actuated to move the chip off the holder and into the appropriate place in the storage rack.

The directing stations may be allocated values, and one or more previously read colours may be programmed as having a respective value. This enables different colour/shades of chips to be used for the same value, and is useful with chips which may be differently coloured on each side.

The apparatus may be programmed to provide statistical information such as how many chips of each colour and/or value have been sorted over a given period.

The apparatus may also be programmed to automatically update previously read colours when the apparatus detects that the colours of corresponding chips gradually changes due for example to the chips becoming dirty and/or fading.

The computer operates in real time to perform this function and means are provided to either accurately control the speed of movement of the chain 40 and/or to detect very accurately this speed. As noted above if the colour of the chip detected does not correspond to any of the colours previously detected during programming, the chip is either ejected into a final column of the rack or is returned into the bin 56.

There is thus described apparatus for sorting gambling chips with a number of advantageous features. The apparatus is wholly programmable and can be programmed by detecting the colour of a variety of chips of the same colour to be able to accurately detect chips of the same colour even with variations due perhaps to dirt, age or any manufacturing variations. Measurement across the whole visible spectrum provides for much more accurate detection and means relatively similar colours can be readily distinguished.

As noted above colour is detected over an area on the chips as the chips move past the detecting apparatus 10. The colour may be detected relative to the position on the chip, during movement thereof, preferably with the colour being detected at a large number of discrete points. The colour read, i.e. intensity and frequency, may be differentiated relative to the position on the chip, i.e. the distance travelled thereby, so as to indicate changes in colour, and the amount thereof. The changes in colour will generally denote boundaries between colours on the chips.

This system is therefore useful with patterned chips, whether random or ordered. In practice only the colour changes will be stored and hence compared. With random patterns, the colour of which previously has generally not been detectable, it would be necessary to initially record all chips for example at a particular casino, at a large number of different orientations.

Apparatus according to the invention could be used to sort a wide. variety of articles other than gambling chips. Furthermore, colour detection apparatus according to the invention could be used in a wide range of other applications. Apparatus according to the invention could be used for example in quality control and perhaps in production to locate extraneous articles. The apparatus could be used to detect colours other than of articles, such as for example of gases or other arrangements. The system measuring colour relative to position is very useful in verifying patterned items such as bank notes.

The detection across the spectra provides for a very accurate and sensitive detection. Furthermore, the detection across the blue end of the spectra in a larger spectra relative to the red end provides for greater sensitivity in this part of the spectrum which is generally more difficult to measure. The programmability of the apparatus obviously makes it particularly flexible.

Whilst endeavouring in the foregoing specification to draw attention to those features of the invention believed to be of particular importance it should be understood that the Applicant claims protection in respect of any patentable feature or combination features hereinbefore referred to and/or shown in the drawings whether or not particular emphasis has been placed thereon.

What is claimed is:

1. Colour detection apparatus for detecting the colour of gambling chips and sorting such chips, comprising:
   a) means for detecting light intensity substantially across the visible spectrum;
   b) means for comparing a read light intensity relative to a previously read light intensity substantially across the visible spectrum;
   c) means for splitting the light into one or more spectra;
   d) means for automatically directing such chips to a required location in response to colour detected; and,
   e) a chip holder into which such chips are delivered, with each colour chip being delivered to a respective part of the holder.

2. Colour detection apparatus for detecting the colour of articles and sorting such articles comprising:
   a) means for detecting light intensity substantially across the visible spectrum;
   b) means for comparing a read light intensity relative to a previously read light intensity substantially across the visible spectrum;
   c) means for splitting the light into one or more spectra;
   d) means for automatically directing such an article to a required location in response to colour detected;
   e) means for automatically supplying articles to the colour detecting apparatus;
   f) a receptacle for such articles from which the supply means takes the articles;
   g) a movable continuous member extending through the receptacle for supplying the articles to the colour detecting apparatus; and,
   h) a plurality of article holders on the continuous member.

3. Apparatus according to claim 2, characterised in that the sorting apparatus comprises a plurality of engagement members respectively operable in response to the colour detected to move an article off a one of the holders such that the article is directed to a respective required location.

4. Apparatus according to claim 3, characterised in that the engagement members are located substantially downstream of the colour detecting apparatus relative to the continuous member.

5. Apparatus according to claim 4, characterised in that the engagement members are located with a plurality of respective receiving areas on the opposite side of the continuous member thereto.

6. Apparatus according to claim 3, characterised in that the engagement members are selectively engageable with sprung pusher members on the article holders for removing an article therefrom.

7. Apparatus according to claim 3, characterised in that an end engagement member is engageable with each article holder downstream of the stations.

8. Apparatus according to claim 7, characterised in that the end engagement member is a collecting member.

9. Apparatus according to claim 8, characterised in that the end engagement member comprises a cam engageable with pusher members on the article holders, said engagement causing the electrostatic charging of the end engagement member.

* * * * *